United States Patent
Legarth (10) Patent No.: US 10,506,823 B2
(45) Date of Patent: Dec. 17, 2019

(54) COMPOSITIONS COMPRISING FERMENTED SEAWEED AND/OR ALGAE

(71) Applicant: Fermentationexperts A/S, Bække (DK)

(72) Inventor: Jens Høffner Legarth, Bække (DK)

(73) Assignee: FERMENTATIONEXPERTS A/S, BÆkke (DK)

( * ) Notice: Subject to any disclaimer, the term of this patent is extended or adjusted under 35 U.S.C. 154(b) by 381 days.

(21) Appl. No.: 14/900,763

(22) PCT Filed: Jun. 26, 2014

(86) PCT No.: PCT/DK2014/050190
§ 371 (c)(1),
(2) Date: Dec. 22, 2015

(87) PCT Pub. No.: WO2014/206419
PCT Pub. Date: Dec. 31, 2014

(65) Prior Publication Data
US 2016/0128357 A1    May 12, 2016

(30) Foreign Application Priority Data
Jun. 28, 2013   (DK) .................................. 2013 70360

(51) Int. Cl.
| C12G 3/00 | (2019.01) |
| A23L 17/60 | (2016.01) |
| C12N 1/20 | (2006.01) |
| C12P 7/10 | (2006.01) |
| C12P 7/56 | (2006.01) |
| A23K 10/12 | (2016.01) |

(Continued)

(52) U.S. Cl.
CPC .............. *A23L 17/60* (2016.08); *A23K 10/12* (2016.05); *A23K 10/18* (2016.05); *A23K 10/30* (2016.05); *C12N 1/20* (2013.01); *C12P 7/10* (2013.01); *C12P 7/56* (2013.01); *A23V 2002/00* (2013.01); *Y02E 50/16* (2013.01); *Y02E 50/17* (2013.01); *Y02P 60/877* (2015.11)

(58) Field of Classification Search
None
See application file for complete search history.

(56) References Cited

U.S. PATENT DOCUMENTS

| 2007/0269555 A1 | 11/2007 | Jensen et al. |
| 2008/0175858 A1* | 7/2008 | Wakabayashi ......... A61K 35/74 424/195.17 |
| 2011/0143012 A1* | 6/2011 | Rettenmaier .......... B01D 53/84 426/648 |

FOREIGN PATENT DOCUMENTS

| CN | 102783582 A | 11/2012 |
| CN | 103039696 A | 4/2013 |

(Continued)

OTHER PUBLICATIONS

Cai et al. (CN 102634490 Aug. 2012 Derwent abstract) 6 pages (Year: 2012).*

(Continued)

*Primary Examiner* — Felicia C Turner
(74) *Attorney, Agent, or Firm* — Morse, Barnes-Brown & Pendleton, P.C.; Sean D. Detweiler, Esq.

(57) ABSTRACT

The present invention relates to compositions comprising fermented seaweed and/or algae. The invention also relates to processes for providing such compositions, wherein the fermentation times are prolonged to increase bioavailability of the nutrients.

9 Claims, 2 Drawing Sheets

(51) Int. Cl.
A23K 10/18 (2016.01)
A23K 10/30 (2016.01)

(56) References Cited

FOREIGN PATENT DOCUMENTS

| | | |
|---|---|---|
| EP | 1 854 469 A1 | 11/2007 |
| JP | 2004-298080 | 10/2004 |
| JP | 2010-252660 | 11/2010 |
| KR | 10-2004-0036997 | 5/2004 |
| WO | WO 2006/123866 * 11/2006 | ............. A23L 1/212 |
| WO | WO 2010/027117 A1 | 3/2010 |
| WO | WO 2012/127004 A1 | 9/2012 |

OTHER PUBLICATIONS

Massholder, Frank "Milchsäuregärung: Konservierung: Definition, Warenkunde, Lebensmittelkunde" Lebensmittellexikon.de, pp. 1-2, XP55410878.
Anhui Wuliangtai Biological Eng Co Ltd—Nov. 21, 2012—Week 201327—XP 002729212.
Fang X—Apr. 17, 2013—Week 201364—XP 002729213.
Dokuritsu Gyosel Hojin Suisan Sogo Kenky—Jan. 7, 2003—XP 002729214.
Wan-Loy, Chu "Potential Applications of Antioxidant Compounds Derived From Algae" Aug. 2011—XP 002729215.
International Search Report for PCT/DK2014/050190 dated Jan. 5, 2015.
Danish Patent and Trademark Office Search Report for Application No. PA 2016 00041 dated Aug. 31, 2016.

* cited by examiner

COMPOSITIONS COMPRISING FERMENTED SEAWEED AND/OR ALGAE

CROSS REFERENCE TO RELATED APPLICATIONS

This application is a U.S. National Phase Application of PCT International Application Number PCT/DK2014/050190, filed on Jun. 26, 2014, designating the United States of America and published in the English language, which is an International Application of and claims the benefit of priority to Danish Patent Application No. PA 2013 70360, filed on Jun. 28, 2013. The disclosures of the above-referenced applications are hereby expressly incorporated by reference in their entireties.

TECHNICAL FIELD OF THE INVENTION

The present invention relates to a composition comprising fermented seaweed. In particular the present invention relates to a food and/or feed product comprising such fermented composition.

BACKGROUND OF THE INVENTION

There is a continued demand in the art for high quality food/feed having improved nutritional characteristics. The challenges are several and include reducing spoilage and the presence of potential pathogenic bacteria and organisms in the food/feed and improving the nutritional characteristics of the food/feed. Fungi are the principal cause of spoilage of livestock feed, particularly in feed comprising legumes. Some fungal species may cause serious disease in livestock consuming the feed by elaborating toxins. Bacterial spoilage may also occur although the problem is in particular in liquid feed. Animal feed may be the source of several pathogens. For example, livestock feed is often delivered to the animals by liquid feeding systems. This causes several problems. Potential harmful bacteria and organisms are natural inhabitants of soil and vegetation and are accordingly found on feed components and everywhere in the animal's surroundings. The bacteria and other organisms present will ferment, unless prevented e.g. by sterilisation. The fermentation may result in outgrow of pathogenic bacteria or various types of yeast and moulds. This uncontrolled growth in the liquid feed may result in illness, malnutrition, diarrhoea, or even death of the animals. Furthermore, animals infected with *Campylobacter* spp. or *Salmonella* spp. may transfer the infection to humans, and therefore it is desirable to avoid such infections in animals.

Providing fermented feed such as fermented liquid feed (WO2008/006382) prepared to contain low levels of pathogenic microorganisms having a low pH (below 4.5) and high levels of lactic acid bacteria and lactic acid has been reported a valid feeding strategy to decrease pathogenic microorganisms counts along the gastrointestinal tract of growing pigs.

WO 2013/029632 discloses a process wherein fermented feed is dried by the use of a spin flash dryer. WO 2008/006382 describes a process for producing homofermented products. Furthermore, it is described that feeding the animals with such products may reduce the risk of infection with *Campylobacter* and *Salmonella* spp. WO 2012/127004 describes a process for producing a protein rich feed.

There is also a continued demand in the art for high quality proteinaceous food/feed and thus continued need for methods for further improving the nutritional characteristics of manufacturing processes for e.g. livestock feed, thereby improving the benefits of feed products derived therefrom to animals consuming them.

Seaweeds are harvested and consumed by people and animals throughout the world. Seaweeds are also harvested or cultivated for the extraction of alginate, agar and carrageenan, gelatinous substances collectively known as hydrocolloids or phycocolloids. Hydrocolloids have attained commercial significance as food additives. The food industry exploits their gelling, water-retention, emulsifying and other physical properties. Agar is used in foods such as confectionery, meat and poultry products, desserts and beverages and moulded foods. Carrageenan is used in salad dressings and sauces, dietetic foods, and as a preservative in meat and fish products, dairy items and baked goods. Other beneficial effects of seaweeds are:

- Seaweed absorbs large volumes of P and N in the seas;
- Seaweed is the protein source of the future. It is possible to produce 1-20 times more protein per hectare than plant protein in agriculture;
- Seaweed contains omega 3 and 6 fatty acids that benefit health.

Hence, an improved process for preparing seaweeds for further use would be advantageous, and in particular, a more efficient and/or reliable feed/food comprising processed seaweeds would be advantageous.

SUMMARY OF THE INVENTION

In one aspect the present invention provides a novel process for breaking down the cell walls of seaweeds. Such process may increase the availability of the protein and/or antioxidant content of seaweeds.

Thus, an object of the present invention relates to a process for pre-processing seaweeds/algae for further use. Another object of the present invention relates to the provision of a process for improving the digestibility of seaweed/algae. A further object is to provide a process for preparing seaweeds/algae for further use e.g. in a process for producing biofuel such as bioethanol and/or antioxidants.

In particular, it is an object of the present invention to provide a process that solves the above mentioned problems of the prior art.

Thus, one aspect of the invention relates to a process for providing a composition comprising fermented seaweeds and/or algae, the process comprising
  a) providing an inoculum comprising essentially lactic acid-producing bacteria;
  b) providing a material comprising seaweeds and/or algae to be fermented;
  c) optionally, providing a source of phytase;
  d) combining the materials of steps a) and b) and optionally c), thereby providing a combinatorial material;
  e) fermenting the combinatorial material of step d) using the inoculum of step a) for a period of at least 15 days;
  f) optionally, drying the fermented combinatorial composition; and
  g) providing a combinatorial composition comprising fermented seaweeds and/or algae.

Another aspect of the present invention relates to a process for providing a composition comprising fermented seaweeds and/or algae, the process comprises:
  a) providing an inoculum comprising essentially lactic acid-producing bacteria;
  b) providing a material to be fermented, where said material comprises seaweeds and/or algae;
  c) optionally, providing a source of phytase;

d) combining the materials of steps a), (b) and optionally c), thereby providing a combinatorial material;
e) fermenting the combinatorial material of step d) using the inoculum of step a);
f) providing a first fermented composition after 2-10 days of fermentation in step d);
g) providing a second fermented composition after at least 15 days of fermentation in step d);
h) optionally, drying the second composition after said 15-40 days and optionally drying the first composition after said 2-10 days, wherein at least part of said first fermented composition provided in step f) is mixed with at least a part of said second composition provided in step g), thereby providing a third fermented composition.

In yet an aspect the invention relates to a process for providing a composition comprising fermented seaweeds and/or algae, the process comprises:
a) providing an inoculum comprising essentially lactic acid-producing bacteria;
b) providing a first material to be fermented, where said material comprises seaweeds and/or algae;
c) optionally, providing a source of phytase;
d) combining the materials of steps a), (b) and optionally c), thereby providing a first combinatorial material;
e) fermenting the first combinatorial material of step d) using the inoculum of step a) for a period of 3-10 days, such as 5-10 days or such as 8-10 days; thereby providing a first fermented composition;
f) combining the first fermented composition of step e) with a plant material to be fermented, wherein said second material comprises at least one proteinaceous plant material having a protein content of at least 20% by weight dry matter, thereby providing a second combinatorial material;
g) fermenting the second combinatorial material of step f), using the first fermented composition of step e) as a inoculum, for a period of at least 5 days, such as 5-12 days, such as 5-10 days, such as 5-7 days or such as 8-10 days; thereby providing a second fermented composition; and
h) optionally, drying the second fermented composition.

In a preferred embodiment, the material to be fermented also comprises rapeseed.

Yet another aspect of the present invention is to provide a fermented composition obtained/obtainable by the processes according to the invention.

Still another aspect relates to a food/feed ingredient comprising the composition according to the invention.

A further aspect relates to a food/feed product comprising the food/feed ingredient according to the invention.

Still another aspect of the present invention relates to the use of the composition according to the invention in the production of biofuel, such as bio-ethanol and/or antioxidants.

The present invention will now be described in more detail in the following.

DETAILED DESCRIPTION OF THE INVENTION

Overall, it has been realized that seaweeds requires a longer fermentation time to make the cell content of e.g. proteins and antioxidants more available compared to fermentation of plant materials. The availability may both be in relation to food/feed but also in processes for production of biofuel and/or extraction of antioxidants. This realization has been implemented in different ways in the present invention First Process for Providing a Composition Comprising Fermented Seaweeds As described above, an aspect of the invention relates to a process for providing a composition comprising fermented seaweeds and/or algae, the process comprising
a) providing an inoculum comprising essentially lactic acid-producing bacteria;
b) providing a material comprising seaweeds and/or algae to be fermented;
c) optionally, providing a source of phytase;
d) combining the materials of steps a) and b) and optionally c), thereby providing a combinatorial material;
e) fermenting the combinatorial material of step d) using the inoculum of step a) for a period of at least 15 days;
f) optionally, drying the fermented combinatorial composition; and
g) providing a combinatorial composition comprising fermented seaweeds and/or algae.

In a preferred embodiment, the provided combinatorial composition comprising fermented seaweeds and/or algae is used a second inoculum for a further fermentation step of preferably plant material.

Second Process for Providing a Composition Comprising Fermented Seaweeds

The prolonged fermentation requirements for seaweeds/algae provides a challenge when it comes to maintaining the probiotic effect of the final product while also maintaining a prolonged fermentation. Thus, a further aspect of the present invention relates to a process for providing a composition comprising fermented seaweeds and/or algae, the process comprises:
a) providing an inoculum comprising essentially lactic acid-producing bacteria;
b) providing a material to be fermented, where said material comprises (preferably fractionized) seaweeds and/or algae;
c) optionally, providing a source of phytase;
d) combining the materials of steps a), (b) and optionally c), thereby providing a combinatorial material;
e) fermenting the combinatorial material of step d) using the inoculums of step a);
f) providing a first fermented composition after 2-10 days of fermentation in step e);
g) providing a second fermented composition after at least 15 days of fermentation in step e);
h) optionally, drying the second composition after said 15-40 days and optionally drying the first composition after said 2-10 days if provided, wherein at least part of said first fermented composition provided in step f) is mixed with at least a part of said second composition provided in step g), thereby providing a third fermented composition.

Preferably the provided first composition and the provided second composition is subsequently (optionally individually dried and) mixed to provide a third composition with novel properties.

By using this process, the probiotic activity is optimized by completing the first fermentation after 2-10 days, whereas the prolonged fermentation (at least 15 days) of the second composition increases the bioavailability of nutrients in the second composition. Thus, the provided third composition has an optimized composition.

Third Process for Providing a Composition Comprising Fermented Seaweeds

It may be advantageously to use the long fermentation time required to open the cell walls of seaweed in a beneficial way, by fermenting seaweeds/algae in a process wherein seaweed and plant materials are fermented partly simultaneously. Thus, yet an aspect of the invention relates to a process for providing a composition comprising fermented seaweeds and/or algae, the process comprises:
  a) providing an inoculum comprising essentially lactic acid-producing bacteria;
  b) providing a first material to be fermented, where said material comprises seaweeds and/or algae;
  c) optionally, providing a source of phytase;
  d) combining the materials of steps a), (b) and optionally c), thereby providing a first combinatorial material;
  e) fermenting the first combinatorial material of step d) using the inoculum of step a) for a period of 3-10 days, such as 5-10 days or such as 8-10 days; thereby providing a first fermented composition;
  f) combining the first fermented composition of step e) with a plant material to be fermented, wherein said second material comprises at least one proteinaceous plant material having a protein content of at least 20% by weight dry matter, thereby providing a second combinatorial material;
  g) fermenting the second combinatorial material of step f), using the first fermented composition of step e) as a inoculum, for a period of at least 5 days, such as 5-12 days, such as 5-10 days, such as 5-7 days or such as 8-10 days; thereby providing a second fermented composition; and
  h) optionally, drying the second fermented composition.

By using the partly fermented seaweed/algae material as an inoculum for fermentation of a plant material having a high protein content a final product is provided with beneficial properties. It has a high protein content constituted of a mixture from several sources and a high digestibility due to the combined fermentation. Again, the required prolonged fermentation period for algae/seaweed is used in a time-optimized way, such that at the end of the process, both the plant material and the seaweed/algae material is fermented for a required period of time.

In addition, the beneficial antioxidants are also made available by the long fermentation of the seaweed/algae.

It is to be understood that the embodiments relating to the first process of the invention also relates to the second process of the invention and third process of the invention and vice versa unless incompatible or if it is specifically mentioned that an embodiment only refers to the first or second process of the invention.

"Inoculation" refers the placement of a microorganism(s) (e.g. lactic acid producing bacteria) that will grow when implanted in a culture medium such as a fermentation tank comprising media to be fermented. "Inoculum" refers to the material used in an inoculation, for example a composition comprising a living organism(s), which is employed to prime a process of interest. For example, an inoculum where the bacteria are essentially lactic acid producing bacteria may be used to direct a lactic acid formation process in a culture medium in a fermentation tank comprising said media (e.g. a feed product). Thus, "to inoculate" refers to the transfer of the inoculum to the media to be processed, for example the transfer of the inoculums to a proteinaceous feed material to be fermented in combination with a source of phytase. The primary inoculum refers to the generation of the initial inoculum in a series of repeated similar of essentially identical inoculation process, for example one or more repetitions of a fermentation process. An aliquot of the product of the formation process may be used to inoculate a new process of fermentation. Thus, the inoculation may be a fermented feed product which comprises viable lactic acid producing bacteria in sufficient amount to prime a lactic acid fermentation process of a another feed product to be fermented. The inoculum may be a in a liquid form, dry form, or essentially dry form. The moisture % of the inoculum may be adjusted in order to optimize the fermentation process. Thus, the inoculum used in the processes of the present invention may be a fermented feed product. In one embodiment the inoculum is provided as essentially pure viable bacteria (such as bacteria in freeze dried form) or bacteria suspended in a suitable media prior to the application (such as a water, buffer or a growth media).

The proportion of the inoculums added to the feed product comprising said protein supplement may vary. In case it is considered that the load of undesirable microbes are significant in the feed product or the fermentation system, the proportion of the inoculum in the fermentation mixture (inoculum+feed product comprising protein supplement+ additional water) may be increased to insure that the fermentation is directed by the microbes (e.g. lactic acid bacteria) of the inoculums. Thus, the inoculum may be provided with a concentration of lactic acid bacteria in the inoculum sufficient to outgrow any bacteria, yeast or moulds present in the product of step (b).

Accordingly, in one embodiment of the invention, the proportion of said inoculum in the combined materials provided in step (d), is in the range of 0.1 to 99.9 vol-%, 1 to 99 vol-%, 5 to 70 vol-%, 10 to 50 vol-%, or 25 to 35 vol-%, 0.1-10 vol-%, or 0.5-5 vol-%, or 1-2.5 vol-%, or around 1-2 vol-vol-%.

The lactic acid bacteria comprise a clade of Gram positive, low-GC, acid tolerant, non-sporulating, non-respiring rod or cocci that are associated by their common metabolic and physiological characteristics. These bacteria, usually found in decomposing plants and lactic products produce lactic acid as the major metabolic end-product of carbohydrate fermentation. This trait has historically linked lactic acid bacteria with food fermentations as acidification inhibits the growth of spoilage agents. Proteinaceous bacteriocins are produced by several lactic acid bacteria strains and provide an additional hurdle for spoilage and pathogenic microorganisms. Furthermore, lactic acid and other metabolic products contribute to the organoleptic and textural profile of a food item. The industrial importance of the lactic acid bacteria is further evidenced by their generally regarded as safe (GRAS) status, due to their ubiquitous appearance in food and their contribution to the healthy microflora of human mucosal surfaces.

In the present invention, the lactic acid-producing bacteria in inoculom used for fermentation are mainly and non-exclusively lactic acid bacteria of the genus *Enterococcus, Lactobacillus, Pediococcus* or *Lactococcus*, or combinations thereof. In one embodiment of the present invention the inoculum comprises at least one lactic acid bacterium species selected from the group consisting of one or more of *Enterococcus* spp., *Lactobacillus* spp., *Lactococcus* spp., and *Pediococcus* spp. In yet a further embodiment of the invention, the lactic acid bacteria are selected from the group consisting of one or more of *Enterococcus faecium, Lactobacillus rhamnosus, Lactobacillus plantarum, Pediococcus acidililactili*, and *Pediococcus pentosaceus*. In further embodiment, the lactic acid producing bacteria are of the order Lactobacillales. The lactic acid-producing bacteria can also be selected from *Lactobacillus* spp., *Pediococcus* spp., *Enterococcus* spp., and *Lactococcus* spp. or a combination thereof. In yet another embodiment, the lactic acid-producing bacteria comprise *Pediococcus pentosaceus*, *Pendiococcus acidilactici* and *Lactobacillus plantarum*, *Lactobacillus rhamnosus*, and *Enterococcus faecium*, or a combination thereof. In still another embodiment, the lactic acid bacteria comprise *Enterococcus faecium* and/or *Lactobacillus rhamnosus*. In a further embodiment, the lactic acid bacteria comprise one or more of *Enterococcus faecium* MCIMB 30122, *Lactobacillus rhamnosus* NCIMB 30121, *Pediococcus pentosaceus* HTS (LMG P-22549), *Pendiococcus acidilactici* NCIMB 30086 and/or *Lactobacillus plantarum* LSI (NCIMB 30083).

In a further embodiment of the invention, the inoculum of step (a) has been obtained by fermentation with primary inoculum comprising at least one lactic acid bacterium species selected from the group consisting of one or more of *Enterococcus* spp., *Lactobacillus* spp., *Lactococcus* spp., and *Pediococcus* spp.

The inoculum of the present invention may be a combination of lactic acid bacteria and industrial by-products. A by-product is a material, which is not the main product of a production process, but a product, which may find use in other processes. An example of a by-product is potato peels. Thus, in an embodiment the inoculum in step a) comprises a mixture of lactic acid bacteria and organic by-products of an industrial process. In yet another embodiment the by-product is potato peels. In a further embodiment the lactic acid bacteria and organic by-products have been mixed directly after the by-products have been generated, thereby minimizing unwanted bacterial contamination. To save energy during the entire process an embodiment of the invention relates to a process wherein no sterilization of the by-products have taken place after the by-products have been generated. By mixing the lactic acid bacteria with the by-product directly after the by-product has been generated unwanted contamination is avoided. In the present context, the term "by-product" refers to products deriving from industrial processes, which may be available at low costs, or for free. Commonly, they are not used directly as feed for animals, and long-time storage may be an issue due to decomposition and uncontrolled fermentation and spoilage. Examples of such "by-products" are whey, spent grain (from brewing, wine or bio-ethanol industry), plant or parts thereof, potatoes, and potato peels.

In a preferred embodiment the by-product(s) have been sterilized during the processing of the main product, thereby making subsequent sterilization steps an unnecessary requirement.

In the present context "sterilization" refers to any process that eliminates (removes) or kills essentially all forms of microbial life, including transmissible agents (such as fungi, bacteria, viruses, spore forms, etc.) present on a surface or in the by-product. Sterilization may be achieved by applying the proper combinations of heat, chemicals, irradiation, high pressure, and filtration. For example during potato peeling at industrial scale the potato peel is loosened from the potato before peeling by steaming. Thus, by mixing the potato peels (by-product) with the lactic acid bacteria directly after the potato peels have been removed from the complete potato no further sterilisation is required later on in the process according to the invention. By "directly after" it is to be understood as within a period, which does not allow e.g. a bacterial fauna of unwanted origin to be established before the lactic bacteria is added to the by-product.

Lactic acid fermentation is the simplest type of fermentation. Essentially, it is a redox reaction. In anaerobic conditions, the cell's primary mechanism of ATP production is glycolysis. Glycolysis reduces—transfers electrons to—NAD+, forming NADH. However, there is only a limited supply of NAD+ available in a cell. For glycolysis to continue, NADH must be oxidized—have electrons taken away—to regenerate the NAD+. This is usually done through an electron transport chain in a process called oxidative phosphorylation; however, this mechanism is not available without oxygen.

Instead, the NADH donates its extra electrons to the pyruvate molecules formed during glycolysis. Since the NADH has lost electrons, NAD+ regenerates and is again available for glycolysis. Lactic acid, for which this process is named, is formed by the reduction of pyruvate.

In heterolactic acid fermentation, one molecule of pyruvate is converted to lactate; the other is converted to ethanol and carbon dioxide. In homolactic acid fermentation, both molecules of pyruvate are converted to lactate. Homolactic acid fermentation is unique because it is one of the only respiration processes to not produce a gas as a byproduct.

Homolactic fermentation breaks down the pyruvate into lactate. It occurs in the muscles of animals when they need energy faster than the blood can supply oxygen. It also occurs in some kinds of bacteria (such as lactobacilli) and some fungi. It is this type of bacteria that converts lactose into lactic acid in yogurt, giving it its sour taste. These lactic acid bacteria can be classed as homofermentative, where the end product is mostly lactate, or heterofermentative, where some lactate is further metabolized and results in carbon dioxide, acetate or other metabolic products.

The process of lactic acid fermentation using glucose is summarized below. In homolactic fermentation, one molecule of glucose is converted to two molecules of lactic acid:

$$C_6H_{12}O_6 \rightarrow 2CH_3CHOHCOOH.$$

The lactic acid bacteria according to the invention may be capable of producing lactic acid and decrease the pH during fermentation to 4.2 or below within 24 hours. In one embodiment, the lactic acid-production should take place within 15 hours.

In heterolactic fermentation, the reaction proceeds as follows, with one molecule of glucose being converted to one molecule of lactic acid, one molecule of ethanol, and one molecule of carbon dioxide:

$$C_6H_{12}O_6 \rightarrow CH_3CHOHCOOH + C_2H_5OH + CO_2$$

Before lactic acid fermentation can occur, the molecule of glucose must be split into two molecules of pyruvate. This process is called glycolysis.

It is preferred that the fermented composition of the present invention is obtained by lactic acid fermentation. It is also preferred that the fermentation is homolactic fermentation directed by homofermentative lactic acid bacteria. In one embodiment, the fermentation is heterolactic fermentation.

The type of seaweed and/or algae may be selected from numerous types of seaweed. In the present context the term "seaweed" encompasses macroscopic, multicellular, benthic marine algae. The term includes members of the red, brown and green algae. Algae are a very large and diverse group of simple, typically autotrophic organisms, ranging from unicellular to multicellular forms, such as the giant kelps that grow to 65 meters in length. Most are photosynthetic and "simple" because they lack the many distinct cell and organ types found in land plants. The largest and most complex marine forms are called seaweeds. Thus, in an embodiment the seaweed/algae in step b) is selected from the group consisting of red, brown and/or green algae. In yet an embodiment the seaweed is *Laminaria saccharina* (sugar kelp) *Laminaria digitata, Laminaria hyperborean* and/or *gracilaria*.

Phytase (myo-inositol hexakisphosphate phosphohydrolase) is a type of phosphatase enzyme that catalyzes the hydrolysis of phytic acid (myo-inositol hexakisphosphate), an undigestable, organic form of phosphorus present in for example grains. A useable form of inorganic phosphorus is released by the hydrolysis of phytic acid. Thus, phytase may increase phosphor uptake when the final composition is used in a feed and/or food.

In an embodiment, the combinatorial product comprises a source of phytase in the form of grain or bran, such as wheat and/or triticale bran. In yet an embodiment the content of said source of phytase is in the range 1-40% by weight, such as 10 to 40% by weight, such as in the range of 10 to 25% by weight, such in the range of 15 to 20% by weight.

The fermentation process in step e) can be controlled by varying e.g. temperature and time to optimize the fermentation reaction. Thus, in yet an embodiment step e) is performed at a temperature in the range 15-45° C., such as 15-40° C., such as 25-35° C., such as 30-40° C., such as 15-20° C. or such as 40-45° C. In another embodiment step e) in the first process of the invention is performed for a period in the range 2-40 days, such as 5-40 days, such as 10-14 days, such as 15-40 days, such as 20-40 days, such as 25-40 days, such as 30-40 days, preferably for at least 15 days, such as at least 30 days, such as at least 100 days, or such as at least 200 days. When the reaction runs for longer periods, the actual fermentation may decrease of cease completely due to lowered viability of the bacteria. However, since enzymatic degradation may continue, it may be advantageous to continue the process. Furthermore, since the pH has been lowered during fermentation, contamination from undesired micro-organisms is minimized.

The compositions of the invention may be dried if the optional drying step of the processes of the invention is employed. In the present context a dry product is to be understood as a product having a water content of 16% or less. Thus, in an embodiment the fermented compositions is dried to a water content not exceeding 16% by weight dry matter such as not exceeding 14% by weight dry matter.

The moisture content of the fermentation step e) may vary. Since seaweeds have a natural high water content directly after harvesting, it is important that the process can run efficiently at high water content. Thus, in yet an embodiment the moisture content during the fermentation step e) is in the range 25-85%, such as in the range 27.5% to 50%, preferably 32 to 38% by weight dry matter (wt %).

In certain instances, it may be advantageous to lower the water content of the seaweeds before the fermentation step e) is initiated. Thus, in an embodiment the moisture content of the seaweeds is lowered to a moisture content below 70% before step e) or during step b), such as to a moisture content below 60%, such as to a moisture content below 50%, such as to a moisture content below 40%, such as to a moisture content in the range 10-40%, such as in the range 20-40%, such as 30-40%. In yet an embodiment the water content is lowered by mechanical means, such as a screw press. In another embodiment the moisture content is lowered by drying, such as by exposure to the sun.

To increase the surface area of the seaweeds during the fermentation step it may also be advantageous to process the seaweeds. Thus, in an especially preferred embodiment the seaweeds are grinded, cut, chopped, sliced, and/or fractionized before or during fermentation. In a specific embodiment the fractionized seaweeds have an average maximum diameter of 5 cm, such as an average maximum diameter of 4 cm such as an average maximum diameter of 3 cm, such as an average maximum diameter of 2 cm, such as an average maximum diameter of 1 cm, such as an average diameter in the range 25 µm to 5 cm, such as 0.1 mm to 5 cm, such as an average diameter in the range of 0.5 mm to 5 cm, such as an average diameter in the range 0.5 mm to 2 cm.

The amount by weight dry matter (wt %) of the seaweed/algae of the combinatorial material in step d may also vary. Thus, in an embodiment the seaweed and/algae material constitutes more than 10% by weight dry matter (wt %) of the combinatorial material in step d), such as more than 17 wt %, such as more than 20 wt %, such more than 22 wt %, such as more than 24 wt %, such as more than 26 wt % such as more than 28 wt % such as more than 30 wt %, such as more than 35 wt %, such as more than 40 wt %, or such as more than 50%, e.g. 10-55%.

As also mentioned for the inoculum it may be advantageous to avoid contamination of the harvested seaweeds/algae by undesired micro-organisms. This may be done by adding inoculum comprising lactic acid bacteria instantly or almost instantly to the harvested seaweeds/algae. Thus, in an embodiment fermentation of the harvested seaweed is initiated within 7 days after harvesting, such as within 6 days, such as within 5 days, such as within 4 days, such as within 3 days such as within 2 days, such as within 1 day, such as within 12 hours, such as within 6 hours, such as 4 hours, such as 2 hours, such as 1 hour such as 30 minutes, such as 10 minutes after harvesting. Preferably the inoculum is added instantly to the harvested seaweeds e.g. emerging the harvested (and e.g. chopped) seaweeds directly into an inoculum. In another embodiment the harvested seaweed is conserved before an inoculum is added. In such instances the harvested seaweed may be stored at least 20 days, such as at least 40 days, such as at least 60 days such as at least 100 days, such as in the range 20-300 days, or such as in the range 20-100 days.

By addition of the lactic acid bacteria the pH in the composition is lowered to a pH of 4.2 or less, e.g. 3.5 or 3.8 due to the controlled fermentation. At these low pH's the risk of contamination from other micro-organisms are limited since they cannot divide under these conditions. Thus, in one embodiment of the invention, the pH of inoculum is below 4.2. In another embodiment, the pH of the inoculum of step (a) is 4.2 or below, such as in the range of 4.2 and 3.5, in the range of 3.9 and 3.7, or 3.8.

In one embodiment, the pH is lowered to a pH in the range 3.5 to 4.2 during fermentation step e) such as to around 3.8.

The content of the different materials in the combinatorial material d) may vary. Thus, in an embodiment the seaweed and/algae material constitutes more than 15% by weight dry matter (wt %) of the combinatorial material in step d), such as more than 17 wt %, such as more than 20 wt %, such more than 22 wt %, such as more than 24 wt %, such as more than wt % such as more than 28 wt % such as more than 30 wt %, such as more than 35 wt %, such as more than 40 wt %.

In a preferred embodiment, the material to be fermented also comprises rapeseed. Rape (or Rapa, oilseed rape, rapa, rappi, rapeseed, canola) (such as *Brassica campestris* and *B. napus*) is a member of the *Brassica* genus, which include cabbage, radish, kale, mustard and cauliflower. Oilseed rapes were grown in India over 3,000 yr ago, and at least 2,000 yr ago in China and Japan. Rape is believed to have originated in the Mediterranean area. Thus, In another embodiment an rapeseed material constitutes more than 15% by weight dry matter (wt %) of the combinatorial material in step d), such as more than 17 wt %, such as more than 20 wt %, such more than 22 wt %, such as more than 24 wt %, such as more than 26 wt % such as more than 28 wt % such as more than 30 wt %, such as more than 35 wt %, such as more than 40 wt %.

The combinatorial material in step d) may comprise further proteinaceous plant materials. Thus, in an embodiment said combinatorial material in step d) comprises at least four independently proteinaceous plant materials, such as at least five independently proteinaceous plant materials or such as at least six proteinaceous plant materials. In yet an embodiment said feed material comprises at least one proteinaceous plant material selected from a leguminous crop or leguminous crop-derived material, where said leguminous crop is selected from the list consisting of lupine, *Vicia faba* (broad bean, field bean), variant of *Vicia faba*, such as *Vicia faba* var. *equina* (horse been), *Pisum sativum*, variants of *Pisum sativum*, such as *Pisum sativum* var. *Arvense* (field pea), *Medicago sativa* (Alfalfa) or variant thereof.

The fermented seaweeds according to the processes of the invention may also be stored for longer periods after fermentation, since the fermentation process may be considered a conservation process in its own right due to the lowering of the pH. The obtained fermented seaweed may also function as a second inoculum, which can be added to further proteinaceous material to be fermented. Preferably, such material is proteinaceous plant material. In an even more preferred embodiment, the further proteinaceous plant material comprises at least two independently proteinaceous plant materials, such as at least three, such as at least four, such as at least five independently proteinaceous plant materials or such as at least six proteinaceous plant materials. In the present context independently plant materials is to be understood as plant materials from different species or variants of plants. In yet an embodiment said feed material comprises at least one proteinaceous plant material selected from a leguminous crop or leguminous crop-derived material, where said leguminous crop is selected from the list consisting of lupine, *Vicia faba* (broad bean, field bean), variant of *Vicia faba*, such as *Vicia faba* var. *equina* (horse been), *Pisum sativum*, variants of *Pisum sativum*, such as *Pisum sativum* var. *Arvense* (field pea), *Medicago sativa* (Alfalfa) or variant thereof. The further material preferably also contains rapeseed, such as meal or cake. Thus, in an embodiment the provided composition comprising fermented seaweeds and/or algae of step g), is mixed with a further proteinaceous source to be fermented, preferably a source comprising one or more sources of protein (as outlined above).

Since seaweed farms of natural reasons often are positioned off-shore it would be advantageous also to be able to perform the fermentation off-shore, since it would otherwise be difficult to initiate the fermentation process before the harvested seaweed/algae starts to decompose due to contamination of undesired micro-organisms. Thus, in an embodiment at least step a) to e) of said process is carried out off-shore, such as on a ship, on a barge, or on a on an offshore platform. It is to be understood that the fermentation process may continue on-shore until a drying process is initiated. Alternatively the ship or barge is emptied directly into a dryer positioned on a harbour. In this way transport of heavy wet fermented products is avoided. In yet an embodiment the fermented seaweed is emptied into a second fermentation area/chamber, wherein the fermented seaweed is added to (and mixed in) the further proteinaceous plant materials to be fermented (as outlined above).

As mentioned above the harvested seaweed may also be conserved off-shore and subsequently the fermentation takes place under controlled conditions in a factory facility.

The optional drying step in the processes according to the present invention may be conducted by different means. In a preferred embodiment, the drying step is performed by a spin flash dryer. To optimize handling, storage and viability of the composition after drying a cooling step may be introduced. Thus, in an embodiment the dried fermented product is cooled instantly after exiting the dryer, such as a spin flash dryer.

Figure 2:
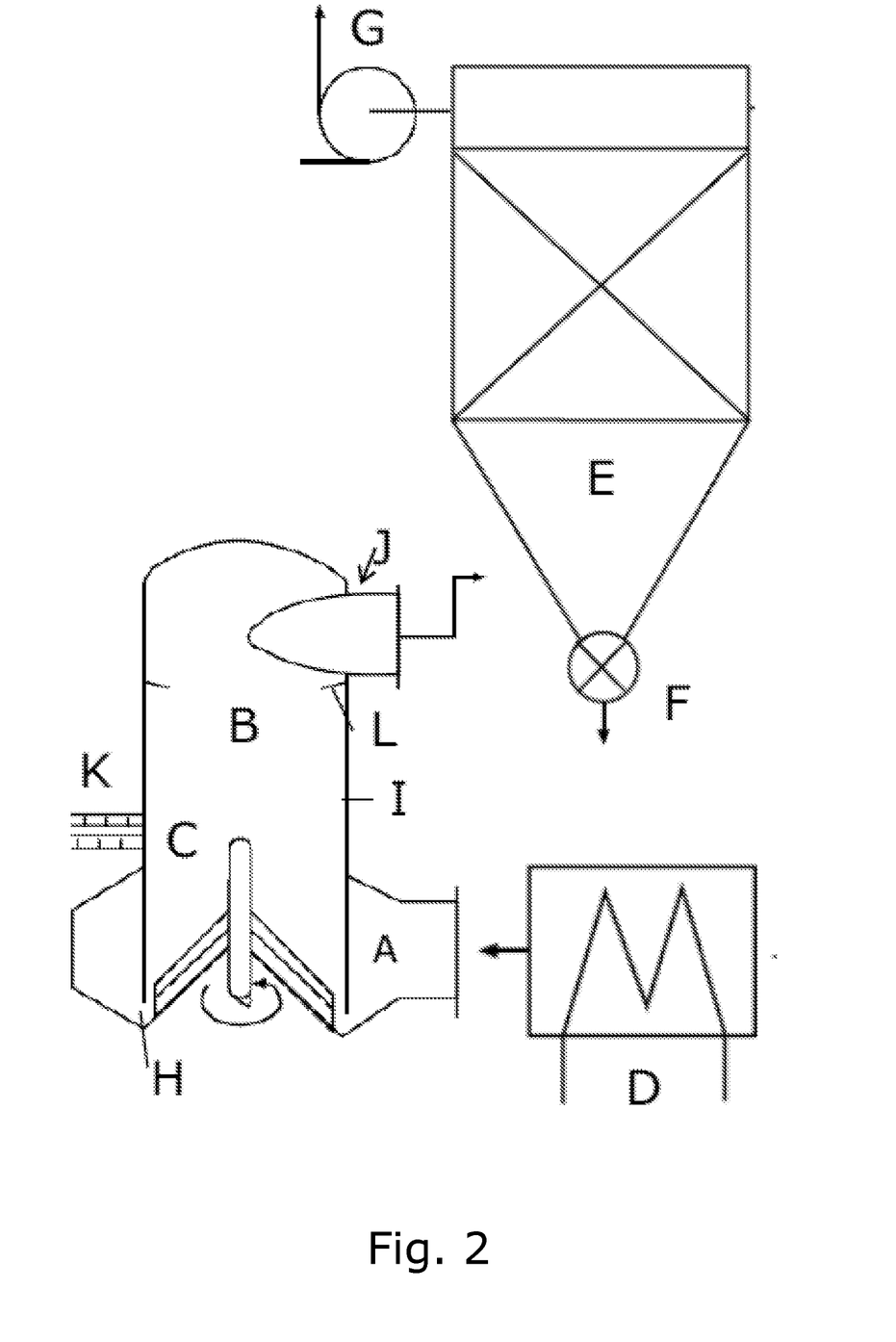
FIG. 2 shows a schematic overview of a spin flash drier.

Reference is made to FIG. 2, which shows schematically and in a 2-dimensional cross sectional view a dryer according to the present invention. The dryer is embodied as a spin flash dryer and comprising a dryer chamber B, formed by cylindrically shaped wall I with a rounded top, inside which drying chamber B the fermented product is dried.

The dryer comprising a drying gas inlet A through which gas at elevated temperature is fed into the dryer chamber B. As indicated in FIG. 2, the drying gas inlet comprises a tube encircling a distal end of the cylindrically shape wall of the dryer B having a diminishing cross section similar in tangential direction to provide an even inflow of drying gas through the slit-shaped opening H provided at the bottom of the cylindrically shaped wall. The inlet A is furthermore arranged so that the drying gas enters into the drying chamber B with a tangential velocity component so as to generate a swirling flow pattern inside the dryer chamber B.

The dryer further comprises a tangentially arranged outlet J through which the dry fermented product leaves the dryer. Fermented product to be dried is transported by the snail transporter K into the drying chamber B above the inlet A. Fermented product introduced into the drying chamber gets in contact with the drying gas swirling inside the drying chamber. The fermented product is typically particulate material and lumps of fermented product above a certain size and weight will, depending on the swirling velocities, be transported upwardly and to the outlet J, whereas heavier lumps of fermented products will fall towards to the bottom of the drying chamber B.

In the bottom of the drying chamber B, a rotor may be provided. The rotor is formed with vanes supporting the swirling motion of the material and gas inside the drying chamber B and cutting heavier lumps of fermented material into smaller lumps, which then will be transported upwardly due to the swirling motion, which also includes an upwardly going velocity component.

The swirling motion will force heavier lumps of material, which are too light to fall to the bottom, upwardly and towards the cylindrically shaped wall of the dryer. To avoid such particles from escaping the drying chamber (as they often are not fully dried due to their relative large sizes), a discriminator L in the form of a downwardly inclined disc is provided below the outlet. The discriminator will force such heavier lumps of material out to the periphery of the drying chamber B where the entrainment velocity is so small that the action of the gravity will transport the lumps of material towards the bottom of the drying chamber and into contact with the rotor, which in turn will cut the lumps into smaller ones.

Dried material leaves the drying chamber A together with gas. A collector E optionally in the form of a cyclone is provide at the outlet J and being operated so that dried fermented material is extracted from the process at the bottom of the collector through a discharge valve F. The flow through the collector may be assisted by an exhaust fan G.

The temperature of the drying gas is elevated by use of the heater D which typically is embodied as a heat exchanger.

The dimensioning of the dryer and the auxiliary elements disclosed in FIG. 2 are made in accordance with the desired capacity of the dryer. Control of the drying process is typically performed by measuring the temperature of the dried fermented product at the outlet J and adjusting the amount of fermented product being fed into the drying chamber to obtain a pre-selected temperature such as maximum 55° C. of the dried material leaving the drier; other process parameters, such as air flow, rotational speed of the rotor C is kept constant while the amount of infeed of fermented product is adjusted to match the preselected temperature at the outlet.

Further, the moisture content in the dried fermented product is advantageously around 10-15 wt % to make it possible for the bacteria to survive in the dried feed.

In further embodiments of the invention the dried, fermented product is cooled instantly after exiting the spin flash dryer and therefore prior to storage. To accomplish this, a cooling section (not shown) is provided downstream of the collector E and may utilize a stream of cold air directed towards and into the dried fermented product. Such downstream cooling element may be in the form of a cyclone. However, other types of cooling elements may also be used. Preferably, the temperature of the air is in the range 5-30° C., such as 10-30° C., such as 15-30° C., such as 5-25° C., such as 5-20° C., such as 10-25° C., such as 15-25° C. Preferably a cooling step is performed very quickly such as within 5 seconds to 5 minutes, such as 10 seconds to 3 minutes, such as 30 seconds to 3 minutes.

Thus, in an embodiment the fermented food/feed ingredient exiting the drying chamber is instantly exposed to a cooling gas with a temperature in the range 5-30° C., such as 5-25° C., such as 10-25° C. or such as 15-25° C. The effect of the cooling step is that the temperature of the product exiting the spin flash dryer is lowered to a temperature in the range 5-30° C., such as 15-25° C. shortly after exiting the spin flash dryer.

The inventors have discovered that this cooling step is important for at least two reasons. Firstly the CFU of the probiotics present in the product is maintained since the viability of the bacteria is heavily impacted if stored at longer periods above 30° C. Another very important effect of the cooling step is the impact on the stored products e.g. when stored in "big bags". If not instantly cooled, the product will aggregate into a large pile and/or form big clumps. Overall, if not instantly cooled the product will be difficult to handle and it may even be difficult to get it out of the storage material wherein it is stored.

Product by Process

The composition obtained/obtainable by the processes of the invention will have a higher digestibility than unfermented seaweed. As shown in example 1, for the fermented seaweeds the cell walls are degraded to a higher extend than for the unfermented seaweeds. Thus, an aspect of the invention relates to a fermented composition obtained/obtainable by the process according to the invention.

Food/Feed Ingredient and Food/Feed Product

The composition obtainable by the processes of the invention may form part of (or be) a food ingredient. Thus, an aspect of the invention relates to a food/feed ingredient comprising the composition according to the invention. In the present context "food" refers to eatable material suitable for human consumption, whereas feed refers to eatable material suitable for animal consumption. The term "animal (s)" as used herein is intended to include mammals such as pigs, piglets, cattle, and horses, poultry such as chickens, turkeys, hens, geese and ducks, and fish such as salmon and trout. Monogastric animals, such as humans, pigs, horses, dogs, and cats, have a simple single chambered stomach. In contrast, ruminant animals or ruminants have a multi-chambered complex stomach. Ruminants digests their food in two steps, first by eating the raw material and regurgitating a semi-digested form known as cud, then eating (chewing) the cud, a process called ruminating. Ruminants include for example cattle, goats, sheep and deer.

The food/feed ingredient may also form part of a food/feed product. Thus, in a further aspect the invention relates to a food/feed product comprising the food/feed ingredient according to the invention.

In yet a further aspect the fermented composition is a pre-composition for use in the production of biofuel, such as bio-ethanol.

An additional aspect relates to the use of the fermented compositions according to the invention in the extraction of antioxidants.

An additional aspect relates to the use of the fermented composition according to the invention as a food/feed ingredient.

Yet an additional aspect relates to a food/feed product comprising the fermented dry feed/food ingredient according to the invention. In an embodiment, the food/feed product comprises in the range 5-50% by weight of the dry feed/food ingredient, such as in the range 5-30%, such as 10-30% or such as 10-20%.

Embodiments for the Second Process of the Invention

Since it is believed that the probiotic effect of the lactic acid bacteria peaks after 2-10 days it is advantageous to provide (and dry) a first composition within that period. The drying step may prolong the viability (CFU) of the lactic acid bacteria. Thus, if the composition is not instantly further processed or used, such drying step may be advantageous. On the other hand, to maximize the improved digestibility of the seaweeds/algae it may be beneficial to let part of the fermentation process continue for a longer period of time, before a second composition is provided (and optionally dried). Said first and second composition may then subsequently be mixed to provide a composition which has been optimized in regard of digestibility, cell wall degradation and probiotic effect. Thus, in an embodiment at least part of said first provided fermented composition is mixed with at least a part of said second provided composition, thereby providing a third fermented composition. The weight/weight ratio of the first composition to the second composition may be in the range 0.1:1-1:0.1, such as 0.3:1-1:0.3, such as 0.5:1-1:0.5, such as 0.7:1-1:0.7, such as 0.8:1-1:0.8, such as around 1:1.

In yet an embodiment the first fermented composition in step f) is provided within 3-7 days, such as 3-5 days. In a further embodiment the second fermented composition is provided in step g) within 15-60 days of fermentation, such as within 15-40 days, such as within 20-40 days, such as within 25-40 days, or such as within 30-40 days of fermentation. In yet an embodiment the second fermented composition is provided after at least 15 days, such as at least 40 days, or such as at least 60 days.

In some specific aspects of the second process of the invention the time for collecting the first and second composition may be different dependent on temperature and the exact components of the composition being fermented. The table below show some specific aspects of the invention in relation to when the first and second composition is provided and optionally dried. For each of the combination in the table below it is to be understood that process may or may not include a drying step according to the invention.

| Provision of first composition (days) | Provision of second composition (days) |
|---|---|
| 2-10 | 11-40 |
| 2-7 | 8-40 |
| 2-5 | 7-30 |
| 5-10 | 11-40 |
| 5-10 | 15-40 |
| 2-7 | 11-30 |
| 2-7 | 8-20 |
| 5-10 | 20-30 |
| Maximum 3 weeks | Up to 20 days |
| Maximum 3 weeks | Up to 50 days |
| Maximum 3 weeks | Up to 100 days |

As previously mentioned the first provided composition may be provided within 2-10 days of fermentation to optimize viability of the lactic acid bacteria. Thus, in an embodiment the concentration of viable lactic acid producing bacteria in said first fermented composition is above $10^7$ CFU per gram, such as in the range $10^8$ to $10^9$ CFU per gram. When the first composition is mixed with the provided second composition a third composition is provided. In yet an embodiment the concentration of viable lactic acid producing bacteria in said third fermented composition is above $10^7$ CFU per gram, such as in the range $10^8$ to $10^9$ CFU per gram.

It should be noted that embodiments and features described in the context of one of the aspects of the present invention also apply to the other aspects of the invention. All patent and non-patent references cited in the present application, are hereby incorporated by reference in their entirety.

The invention will now be described in further details in the following non-limiting examples.

EXAMPLES

Example 1

Figure 1:
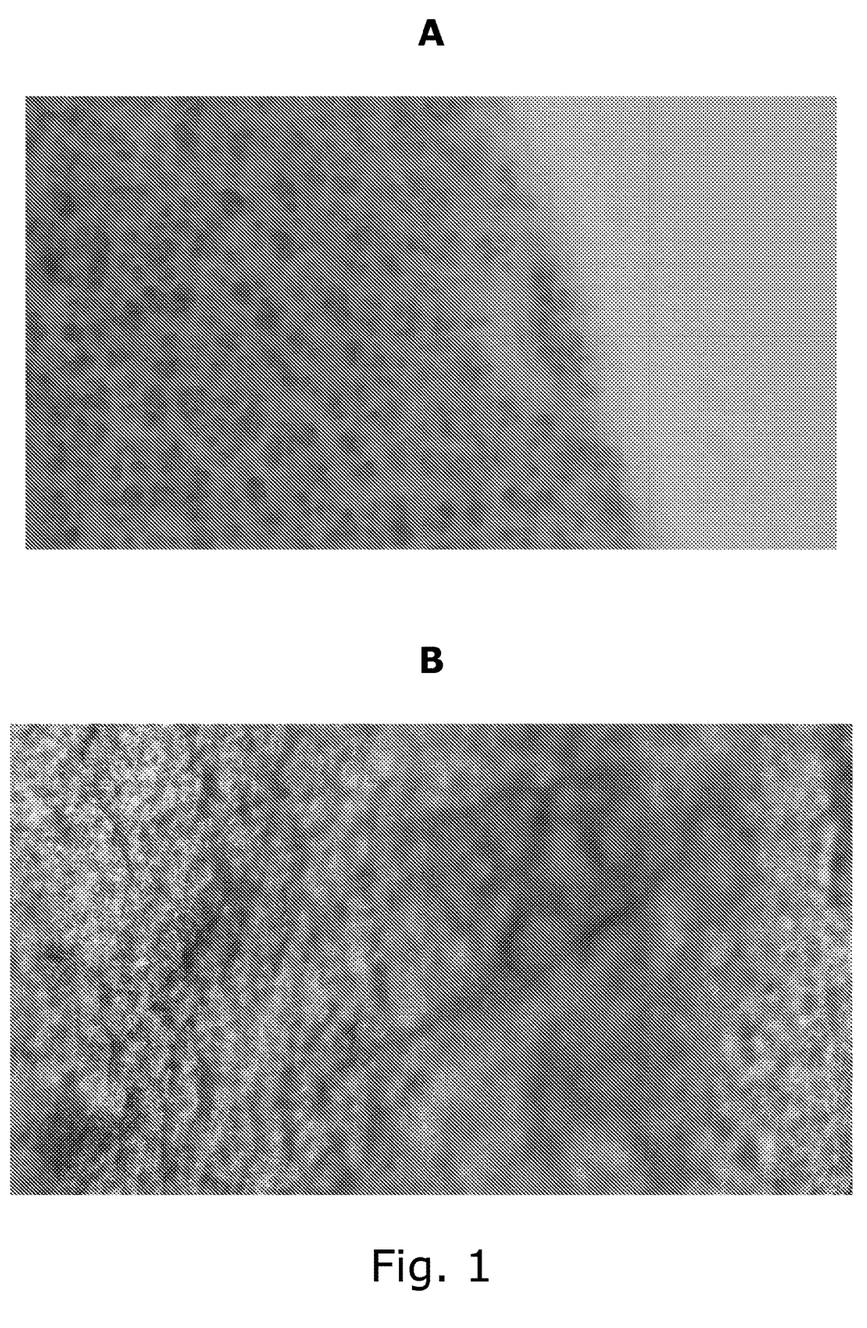
FIG. 1 shows seaweeds fermented for 0 days (FIG. 1A) and seaweeds fermented for 30 days (FIG. 1B).

Prolonged Fermentation of Seaweed
Material and Methods
Compositions comprising seaweeds (*Laminaria saccharina*) were fermented for 0 and 30 days respectively and samples were analysed by microscope before and after the process. The temperature was approximately 20° C.
Results
FIG. 1 shows pictures of seaweeds before and after fermentation process. FIG. 1A) Not fermented; FIG. 1B) fermented for 30 days at 20° C. Though difficult to show in pictures, the cell walls of the seaweed after 30 days of fermentation was clearly decomposed compared to the untreated sample.
It is noted that a heating test to 65° C. for 15 minutes did not break down the cell walls significantly.
Conclusion
By fermenting the seaweed for 30 days the cell walls of the seaweeds are degraded thereby increasing the digestibility.

Example 2

Compositions comprising seaweeds (*Laminaria saccharina*) were fermented for 15 days and samples were analysed by microscope before and after the process. The temperature was approximately 30° C.
The results showed that at a temperature of 30° C. for 15 days of fermentation resulted in breakdown of the cell walls (data not shown).

The invention claimed is:
1. A process for providing a composition consisting essentially of lactic acid-producing bacteria, fermented seaweed and/or algae, and fermented *brassica* genus plant material, the process comprises:
  a) providing an inoculum consisting essentially of lactic acid-producing bacteria, or consisting essentially of lactic acid-producing bacteria and one or more industrial by-products, wherein the microbes in the inoculum consist of lactic acid producing bacteria;
  b) providing a first material to be fermented, where said first material comprises seaweed and/or algae;
  c) optionally, providing a source of enzyme;
  d) combining the materials of steps a), b) and optionally c), thereby providing a first combinatorial material;
  e) fermenting the first combinatorial material of step d) using the inoculum of step a) for a period of 3-10 days; thereby providing a first fermented composition;
  f) combining the first fermented composition of step e) with a second material to be fermented, wherein said second material comprises *brassica* genus plant material, thereby providing a second combinatorial material;
  g) fermenting the second combinatorial material of step f), using the first fermented composition of step e) as an inoculum, for a period of at least 5 days; thereby providing a second fermented composition; and
  h) optionally, drying the second fermented composition; thereby providing a composition consisting essentially of lactic acid-producing bacteria, fermented seaweed and/or algae, and fermented *brassica* genus plant material; wherein the seaweed is fractionized and wherein the fractionized seaweed has an average maximum diameter in the range of 25 μm to 5 cm.
2. The process according to claim 1, wherein the inoculum of step a) is provided with a concentration of lactic acid bacteria sufficient to outgrow any bacteria, yeast or mold present in the first material to be fermented.
3. The process according to claim 1, wherein the proportion of said inoculum in the combined materials provided in step (d), is in the range of 0.1 to 5 vol-%.
4. The process according to claim 1, wherein step e) is initiated within 7 day after harvesting of the seaweed and/or algae.
5. The process according to claim 1, wherein step e) is initiated within 1 day after harvesting of the seaweed and/or algae.
6. The process according to claim 1, wherein the fermentation is carried out off-shore.
7. The process according to claim 1, wherein the inoculum consists essentially of a combination of lactic acid bacteria and one or more industrial by-products.
8. The process according to claim 1, wherein step e) is performed at a temperature in the range of 15-45° C.
9. The process according to claim 1, wherein the seaweed and/or algae material constitutes more than 10% by weight dry matter (wt %) of the combinatorial material in step d).

* * * * *